United States Patent
Kuslich et al.

(10) Patent No.: US 6,620,162 B2
(45) Date of Patent: Sep. 16, 2003

(54) DEVICE FOR INSERTING FILL MATERIAL PARTICLES INTO BODY CAVITIES

(75) Inventors: Stephen D. Kuslich, Stillwater, MN (US); Francis Peterson, Prescott, WI (US); Joseph E. Gleason, Eagan, MN (US)

(73) Assignee: Spineology, Inc., Stillwater, MN (US)

( * ) Notice: Subject to any disclaimer, the term of this patent is extended or adjusted under 35 U.S.C. 154(b) by 0 days.

(21) Appl. No.: 09/909,668

(22) Filed: Jul. 20, 2001

(65) Prior Publication Data

US 2003/0018292 A1 Jan. 23, 2003

(51) Int. Cl.[7] ................................................. A61F 5/04
(52) U.S. Cl. .................. 606/53; 623/17.11; 604/60; 222/200
(58) Field of Search ..................... 606/53, 92, 93, 606/94; 604/59, 60, 62, 63, 64; 623/17.11, 17.16; 222/200, 204

(56) References Cited

U.S. PATENT DOCUMENTS

| 834,261 | A | * | 10/1906 | Chambers |
|---|---|---|---|---|
| 1,347,622 | A | * | 7/1920 | Deininger |
| 2,659,369 | A | * | 11/1953 | Lipman |
| 5,549,679 | A | | 8/1996 | Kuslich ........................ 623/17 |
| 5,571,189 | A | | 11/1996 | Kuslich ........................ 623/17 |
| 5,702,454 | A | | 12/1997 | Baumgartner ................. 623/17 |
| 6,171,312 | B1 | | 1/2001 | Beaty ............................ 606/80 |
| 6,340,299 | B1 | * | 1/2002 | Saito |
| 6,387,130 | B1 | * | 5/2002 | Stone et al. .............. 623/17.16 |

FOREIGN PATENT DOCUMENTS

| DE | 1223495 | | 8/1966 |
|---|---|---|---|
| DE | 4409836 | A1 | 9/1995 |
| EP | 0621020 | A1 | 3/1994 |
| FR | 2287894 | | 5/1976 |

OTHER PUBLICATIONS

U.S. patent application Ser. No. 60/256,014, Stephen Kuslich, filed Dec. 15, 2000.

* cited by examiner

*Primary Examiner*—Ralph A. Lewis
(74) *Attorney, Agent, or Firm*—Vidas, Arrett & Steinkraus, P.A.

(57) ABSTRACT

An instrument for filling cavities in a body, such as a cavity within a reamed out spinal disc, with beads includes a cyclical agitator that functions to prompt the introduction of one bead at a time through the fill tube to prevent clogging and to promote compaction within the cavity.

20 Claims, 8 Drawing Sheets

DEVICE FOR INSERTING FILL MATERIAL PARTICLES INTO BODY CAVITIES

CROSS-REFERENCE TO RELATED APPLICATIONS

Not Applicable

BACKGROUND OF THE INVENTION

1. Field of the Invention

This invention relates to a medical instrument for filling a cavity formed within bone, a spinal disk, or a fixation device inserted therein, with biocompatible beads. More specifically, the present invention is directed to a vibratory tool having a reservoir of biocompatible material in fluid communication with a proximal end of a tubular injection cylinder, the injection cylinder and reservoir are vibrated to cause the material to pass from the reservoir into the proximal end of the injection cylinder. The vibratory action of the device and gravity allow the material to pass through the injection cylinder to its distal end and be deposited into a delivery site. The vibratory action of the injection cylinder causes the distal end of the cylinder to gently tap the deposited material thereby compacting the material within the delivery site. The unique construction and vibratory action of the present device prevents fill material from plugging the device during use and provides for a consistent flow of fill material into the delivery site.

2. Description of the Related Art

Bioceramic compounds and other types of fill material such as bone may be used as a fill material in the treatment of certain orthopaedic conditions; including fractures, non-unions, tumors, and cysts and as an adjunct to certain fusion procedures. In general, these conditions involve filling a cavity that has been created by the pathology itself or by the action of the surgeon during removal of the pathology.

The cavity may be filled by the placement of a block of fill material or by the gradual addition of granules of fill material such as bioceramic beads, crushed bone or a combination thereof. Alternatively, a variety of different types of support and/or joining devices may be inserted into the cavity. These devices may be filled with the fill or graft material, as opposed to directly filing the cavity therewith.

Devices such as those used in spinal fixation are well known in the art. Such devices may include apparatuses which are inserted into hollowed out portions of a spinal disk or vertebrae. For example, U.S. Pat. No. 5,549,679 issued Aug. 20, 1996 and U.S. Pat. No. 5,571,189 which issued Nov. 5, 1996, both of which being incorporated in their entirety herein by reference, disclose an expandable fabric bag and method for stabilizing a spinal motion segment. In these patents, a damaged disc is reamed out and an expandable fabric bag is inserted into the cavity thus formed. Bone graft material is then inserted into the bag to fill and expand the bag such that the filled bag will take the place of the reamed out disc. Over time, the material within the bag will cause a fusion of the adjacent vertebrae. The bag filling is through an opening which is closed off after filling.

Another device and method for stabilizing a spinal motion segment is described in co-pending U.S. Provisional App. No. 60/256,014 filed Dec. 15, 2000, the entire contents of which being incorporated herein by reference. In this Application a band of fabric or mesh is inserted into a reamed out cavity within a disk or other spinal body. The fabric of the band may be structured to allow a bone graft fill tool to penetrate the band, without causing it damage, and deposit fill material into the area defined by the band and surrounding tissue.

These and other devices are intended to provide support to the spinal segment which they are being inserted into and to encourage fusion of the surrounding spinal bodies through the device. A key aspect to such devices is the proper placement and compaction of bone graft material into the site through which bone growth and eventual fusion is to take place.

As indicated above the cavity or device may be filled with material in a variety of different manners. Manual filling such as by insertion by hand of one or more chunks of fill material may not provide for ideal filling and compaction characteristics which may be essential to encouraging proper bone growth and fusion. The use of granular material in gradually filling the cavity, or a device inserted therein has the advantage of allowing filling through a smaller entrance portal. In addition, by gradually filling the cavity or device with granular fill material allows the cavity to be filled in a more uniform and complete manner.

In use however, granular material such as ceramic granules tend to jam within injection tubes and tend to break apart and pulverize when injection and/or impaction forces are vigorously applied. Broken or pulverized granules of bioceramic compounds contain fine dust particles that have been shown to inhibit bone growth.

The granules may exist in a variety of shapes and sizes, such as, for example amorphous chunks or solid geometric shapes. Of the various available granule shapes, spherical shaped beads provide several potential advantages over other granular shapes. Notably, spherical beads may provide maximal and consistent inter-granule porosity and improved flowability. However, even spherical granules are known to jam and break apart during the injection procedure. Therefore, there is a need for a new method of granule injection that is easier, faster, and produces less jamming and granule breakage.

Experiments have been conducted with various means to more efficiently and effectively introduce granular material into cavities. The goal of these experiments was to develop a novel means for improving spherical granule flow while minimizing the breakage of granules. As a result of these experiments the device of the present invention was constructed. The present device was determined to provide the best combination of flow efficiency and the least tendency toward granule breakage during the fill process. By utilizing the present invention for inserting bioceramic beads or other fill material into a body cavity, the invention may improve the care of patients with certain orthopaedic conditions.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

The entire content of all of the patents listed within the present patent application are incorporated herein by reference.

BRIEF SUMMARY OF THE INVENTION

In light of the above, the present invention is directed to a method and apparatus which provides for improved filling and compaction of bone graft material within a hollowed portion of a bone, spinal segment or a fixation device positioned therein.

In at least one embodiment, the present invention is directed to a filling instrument that directs one granule or bead to drop into a tube from a bead reservoir, upon dropping a bead into the tube, the tube and reservoir are pneumatically actuated to pop back up to unblock the granules therein, which in turn allows another bead or granule to drop into the tube in repeating cycles. The present device agitates the granules at each stroke so they fill up the tube. The up and down motion of the tube and reservoir also provides for compaction of the beads at the distal end of the tube which may compact the beads into the chamber or spinal fixation device being filled.

The present invention allows the surgeon to fill body cavities more easily and completely, with less damage to granules, and through a very small entrance portal. The invention also provides a means to compact the granular mass, thereby improving the fill density and the stability of the granular pack.

The invention provides for a bead reservoir that is submitted to vibratory energy that encourages the bead pack to flow into a hollow, tubular injection cylinder. Pneumatic, hydraulic, or other mechanical forces then cause the injection cylinder to oscillate along its longitudinal axis, while the beads are gently pushed into the cavity by a combination of frictional forces against the cylinder walls and the pull of gravity.

Once the cavity is filled or nearly filled, the distal tip of the oscillating cavity gently taps the top of the bead pack, thereby forcing the beads into a more densely packed construct.

As indicated above, one application of the invention is in the field of spinal surgery. Surgeons often attempt to fill certain spaces within the spine with bone or bone substitute materials, such as bioceramic material. The filled spaces then provide mechanical support and the proper milieu for bone ingrowth. The local spinal anatomy restricts safe access to certain internal spinal areas. Therefore, surgeons are often required to operate through very small entry portals. The present invention provides the surgeon with a reliable and effective device suitable for filling cavities deep within the spine, e.g. the interbody or intra-vertebral spaces.

One particularly common spinal procedure is known as an interbody fusion. In the interbody fusion procedure, the surgeon attempts to fill the gap between two opposing vertebrae with a material and/or device that supports load and encourages bony ingrowth. Such devices include, but are not limited to, those described in U.S. Pat. Nos. 5,489,308; 5,549,679; 5,571,189 and others.

As shall be made clear from the description below, in at least one embodiment of the invention, the present device may be inserted through very small diameter tubes. As a result, it is possible to fill the intervertebral space with little or no retraction of sensitive local nerves and vessels. For example, this invention allows the surgeon to fill the interbody space through a portal substantially smaller than currently required for many procedures.

Another area where the present invention may be of use would be in procedures known as vertebra-plasties or kypho-plasties, wherein the surgeon attempts to fill the area occupied by a so-called "compression fracture" of the vertebral body. The present invention could be used to fill this area through the narrow confines of the vertebral pedicle or through a small (about 3–10 mm) hole in the side or front of the vertebral body. As a result, use of the invention would reasonably reduce risk and complications compared to other procedures that require a larger exposure, as in the case of the placement of large bioceramic blocks.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

With reference to the FIGS. 1–8 wherein identical elements are numbered identically throughout, an embodiment of the inventive filler instrument, indicated generally at 10, is shown. In the embodiment shown, the filler instrument 10, has three primary portions: a central housing 12, a tubular injection cylinder or needle 14 and a reservoir 16.

Figure 2:
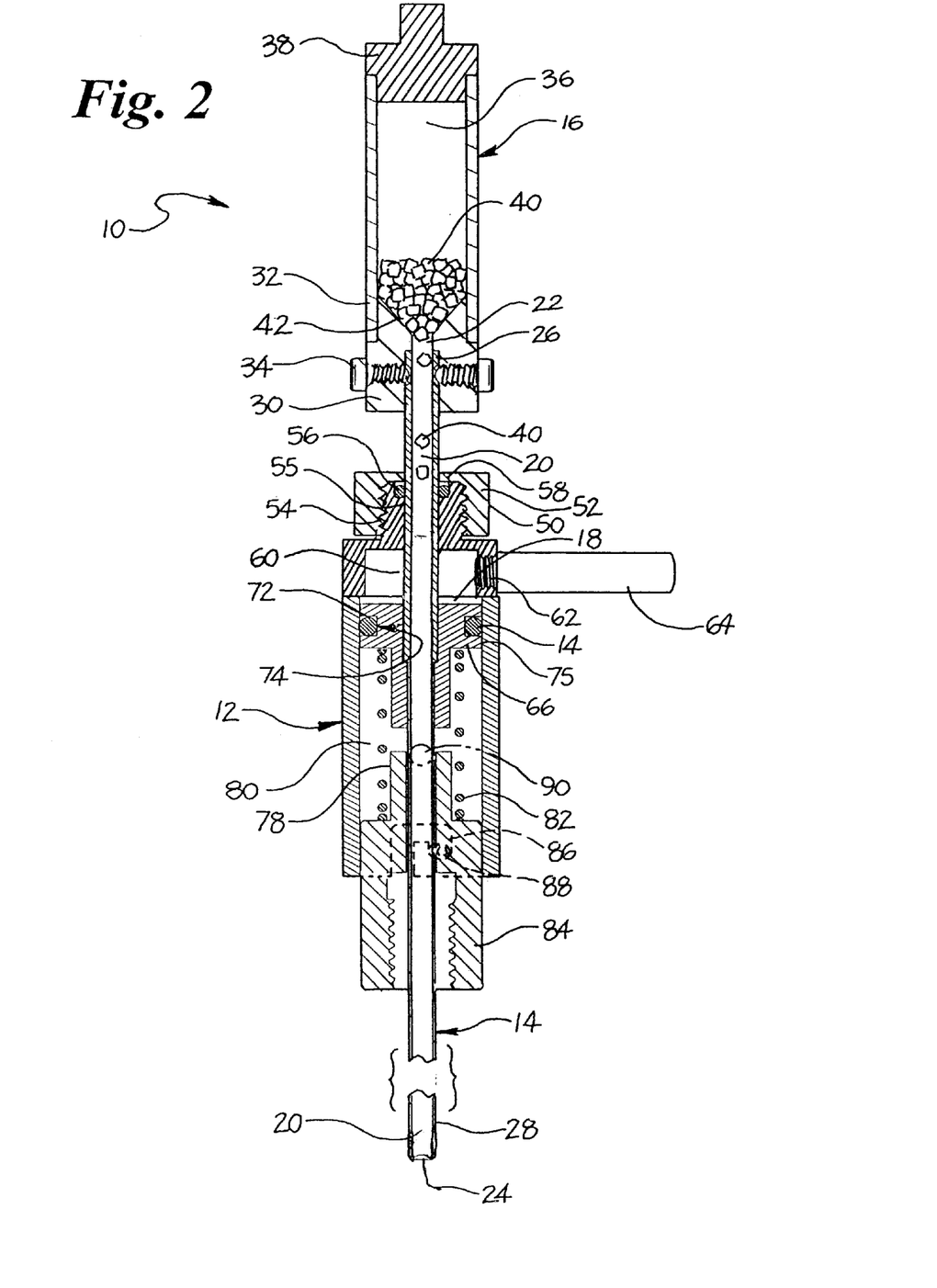
FIG. 2 is a longitudinal sectional view of the embodiment of the invention shown in FIG. 1.

As is shown in FIG. 2, the needle 14 defines a hollow needle chamber or passage 20 which includes a proximal opening 22 at proximal end 26 and a distal opening 24 at distal end 28. The needle chamber 20 has a diameter sufficient to allow passage of a bioceramic bead or other particle of material 40 to pass therethrough in a single-file line or individually.

Typically, the needle passage 20 and openings 22 and 24 will be approximately 0.5 mm to 5 mm in diameter. The proximal opening 22 of needle 14 is in fluid communication with the reservoir 16. The reservoir may contain the fill material 40 such as bioceramic beads or other materials. The individual particles of material 40 are sized to be able to enter the proximal opening on a one-at-a-time basis and pass through the passage 20 in a single file line when the device 10 is activated.

The central housing 12, defines a central passage or chamber 18 (as may best be seen in FIG. 6) through which the needle 14 may travel longitudinally therein. The proximal end 26 extends proximally beyond the housing 12 and passage 18 and is engaged to the reservoir 16. The reservoir 16 is defined by a reservoir housing 32. The reservoir housing 32 is engaged to the proximal end 26 of the needle 14 by a mounting collar 30. The mounting collar 30 employs one or more fastening members 34 to retain the proximal end 26 of the needle 14 therein. The fastening members 34 may be any type of fastener such as a screw, bolt, clip, etc. The mounting collar 30 may be engaged to the reservoir housing 32 by any of a variety of mechanisms. For example: the collar 30 and reservoir housing 32 may be opposingly threaded to allow the collar to be screwed into the reservoir housing 32, the collar 30 may be sized to fittingly engage the reservoir housing 32, the collar 30 may snap-fit into the reservoir housing, etc.

Figure 3:
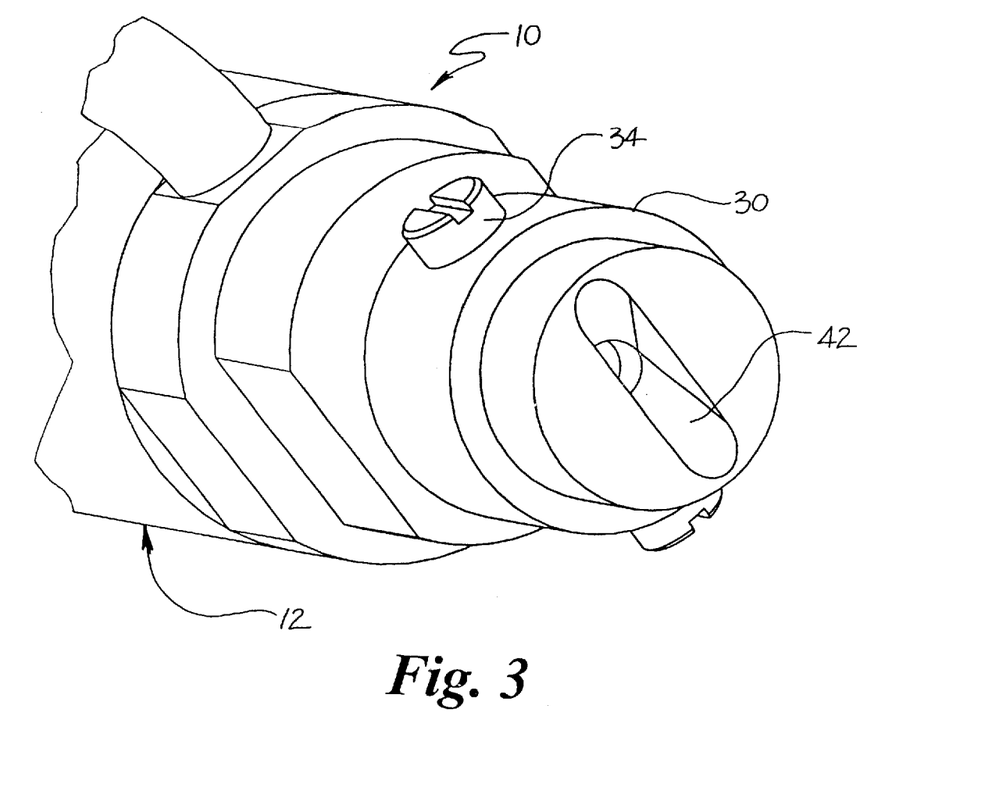
FIG. 3 is an enlarged view of the angled opening slot joining the reservoir and the injection cylinder of the embodiment of the invention shown in FIG. 1.
Figure 4:
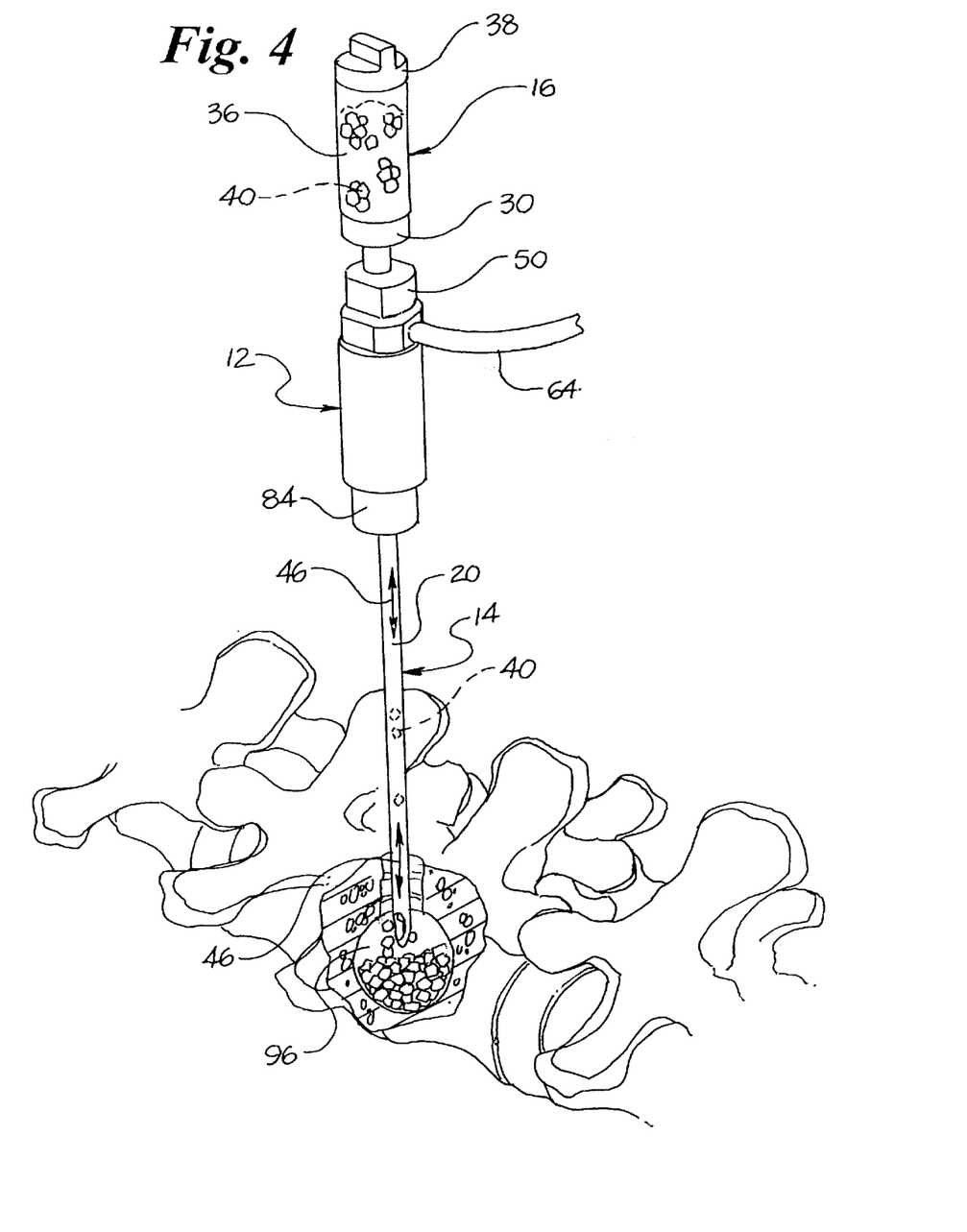
FIG. 4 is a perspective view of an embodiment of the invention as shown in its intended environment of use.
Figure 5:
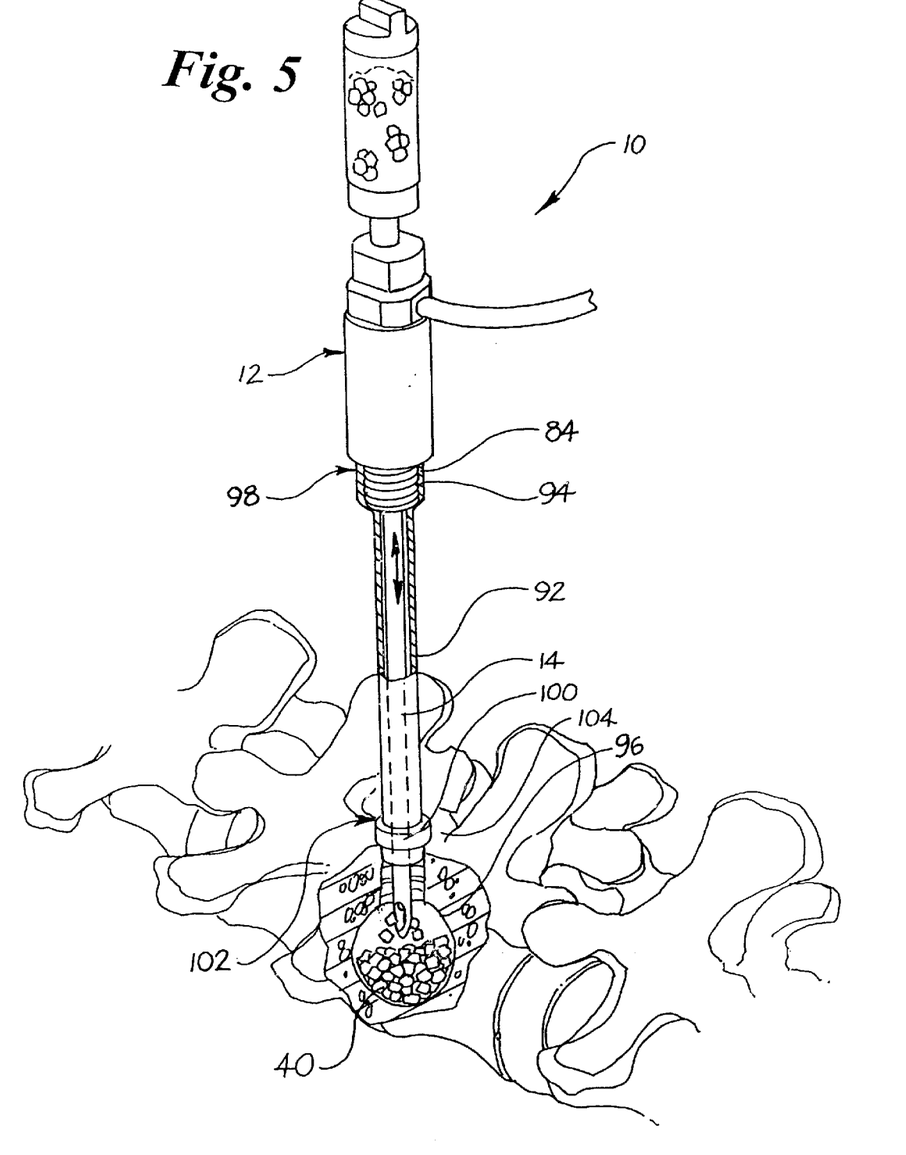
FIG. 5 is a perspective view of an embodiment of the invention as shown in its intended environment of use.

As may best be seen in FIG. 3, the collar 30 includes an angled opening slot 42. The slot 42 is designed to allow beads to pass into the proximal opening 22 of the needle chamber 20 on a one-at-a-time basis such as is depicted in FIGS. 2 and 4. The unique configuration of the opening slot 42 helps to prevent beads or other fill material from blocking the proximal opening 22 as well as prevent multiple beads or particles from plugging the needle chamber 20. In addition, by providing a slot 42 which regulates bead flow into the needle chamber 20, the present device provides a user with a significant degree of control for placement of the beads in a delivery site, such as is illustrated in FIGS. 4–5.

Returning to FIG. 2, the reservoir housing 32 defines a reservoir chamber 36 which may be filled in-whole or in-part by a predetermined number or volume of fill material 40. The reservoir housing 32 may be at least partially transparent to allow a user to see the material 40 within the reservoir chamber 36. The reservoir housing 32 may also include volume indicators or markings so that the volume of material 40 remaining within the chamber 36 may be readily determined at any time.

As indicated above, the fill material 40 may be comprised of bone graft material, bioceramic beads, crushed bone, and/or other types of biocompatible fill material. The reservoir housing also includes a reservoir plug or seal 38 which may be readily removed from the reservoir housing 32 to allow the fill material 40 to be inserted therein, and may be engaged to the reservoir housing 32 to prevent spillage of the fill material 40 therefrom. When secured to the reservoir housing 32, the seal 38 also acts to prevent the introduction of contaminants into the reservoir housing 32.

The needle 14 extends from the reservoir 16 into the passage 18 of the central housing 12. Prior to entering the passage 18, the needle 14 passes through a proximal valve assembly 50, which provides a sliding valve seal 55 between the needle 14 and central housing 12. The proximal valve assembly may comprise a nut, ring or other type of retaining member 52 which is secured to a proximal valve receiving member 54 of the housing 12. The retaining member 52 and receiving member 54 may be reversibly threaded to allow the retaining member 52 to be threaded onto the receiving member 54, or they may be otherwise constructed to provide removable engagement therebetween.

The retaining member 52 includes an inner radial lip 58 which defines an opening through which needle 14 is passed. The radial lip 58 provides a surface upon which an o-ring 56 may be positioned. When the retaining member 52 is screwed or otherwise fastened on to the receiving member 54, the o-ring 56 is sandwiched between the radial lip 58 and the receiving member 54, there by providing a first or proximal sliding valve seal 55 between the housing 12 and the needle 14.

As is best shown in FIG. 2, the proximal seal assembly 50 defines the proximal end of a piston chamber 60. The piston chamber 60 includes a fluid entrance port 62 which is connected to a fluid line 64 and source 44 shown in FIG. 8. The fluid source may be hydraulic, pneumatic, or any other means for providing liquid or air based pressure into the chamber 60. Turning to the close-up view shown in FIG. 7, the piston chamber 60 includes a piston member 66 which extends outward from the needle 14 to the inner wall 68 of the chamber 60. The piston member 66 may be integral with the needle 14 or may be a separate apparatus through which the needle 14 is passed through and sealed therein.

Figure 7:
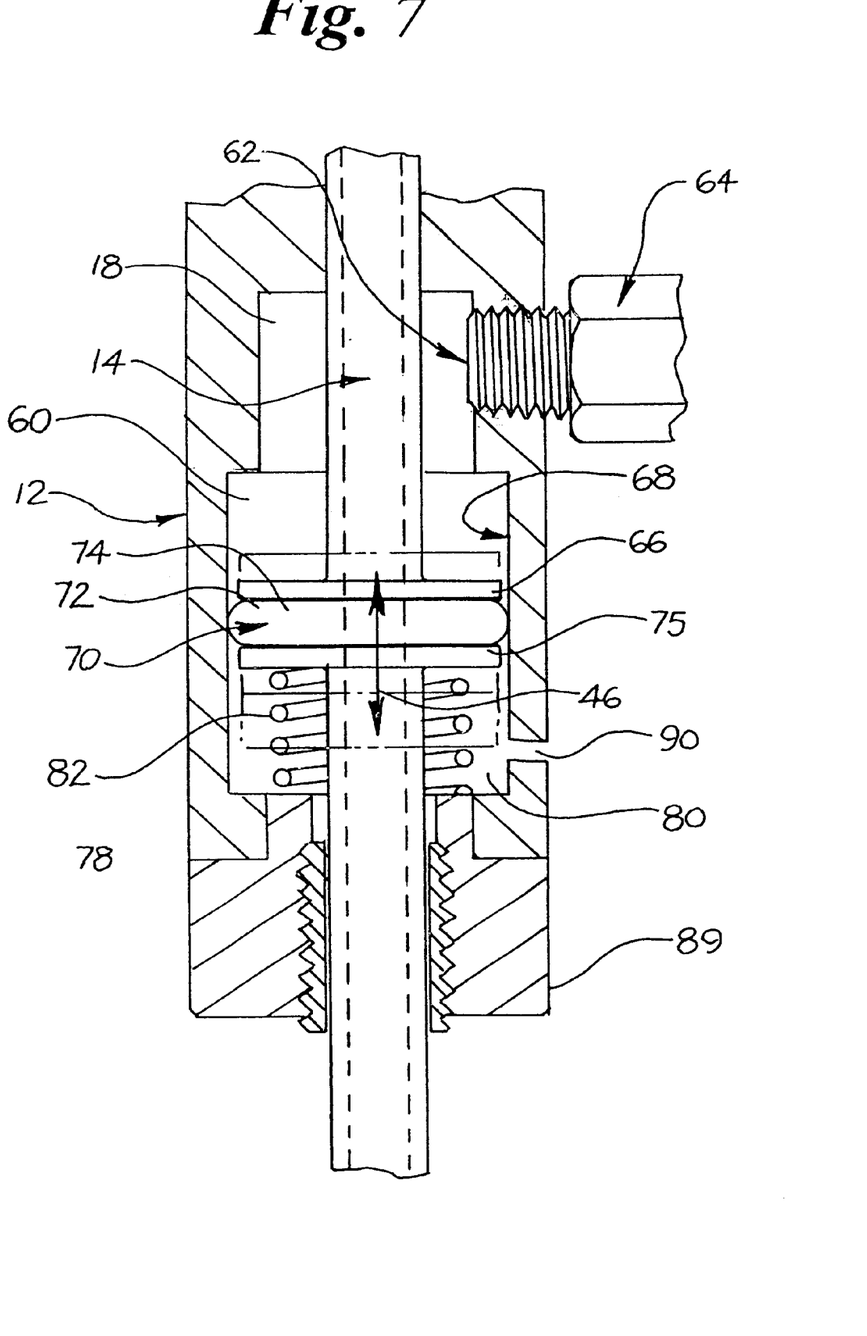
FIG. 7 is a detailed sectional view of portions of the housing of an embodiment of the invention.

The piston member 66 includes a groove or notch 70 about its circumference 72. The notch 70 provides a space in which a piston o-ring 74 is placed. The piston o-ring 74 extends beyond the piston member 66 to contact the wall 68. The presence of the piston o-ring 74 between the piston member 66 and the wall 68, effectively provides a second or distal sliding valve seal 75 between the needle 14 and the housing 12.

Referring to FIG. 7, when a fluid is injected into the piston chamber 60 from fluid line 64, fluid pressure will build within the chamber and press against the piston member 66. The arrangement of the first and second sliding seals 55 and 75 respectively allow the building pressure to move the piston member 66, and thus the needle 14, longitudinally in the distal direction. The distal movement of the piston member 66 and needle 14 is limited by the presence of a break or stop 78. The stop 78 shall be discussed in greater detail below.

Figure 1:
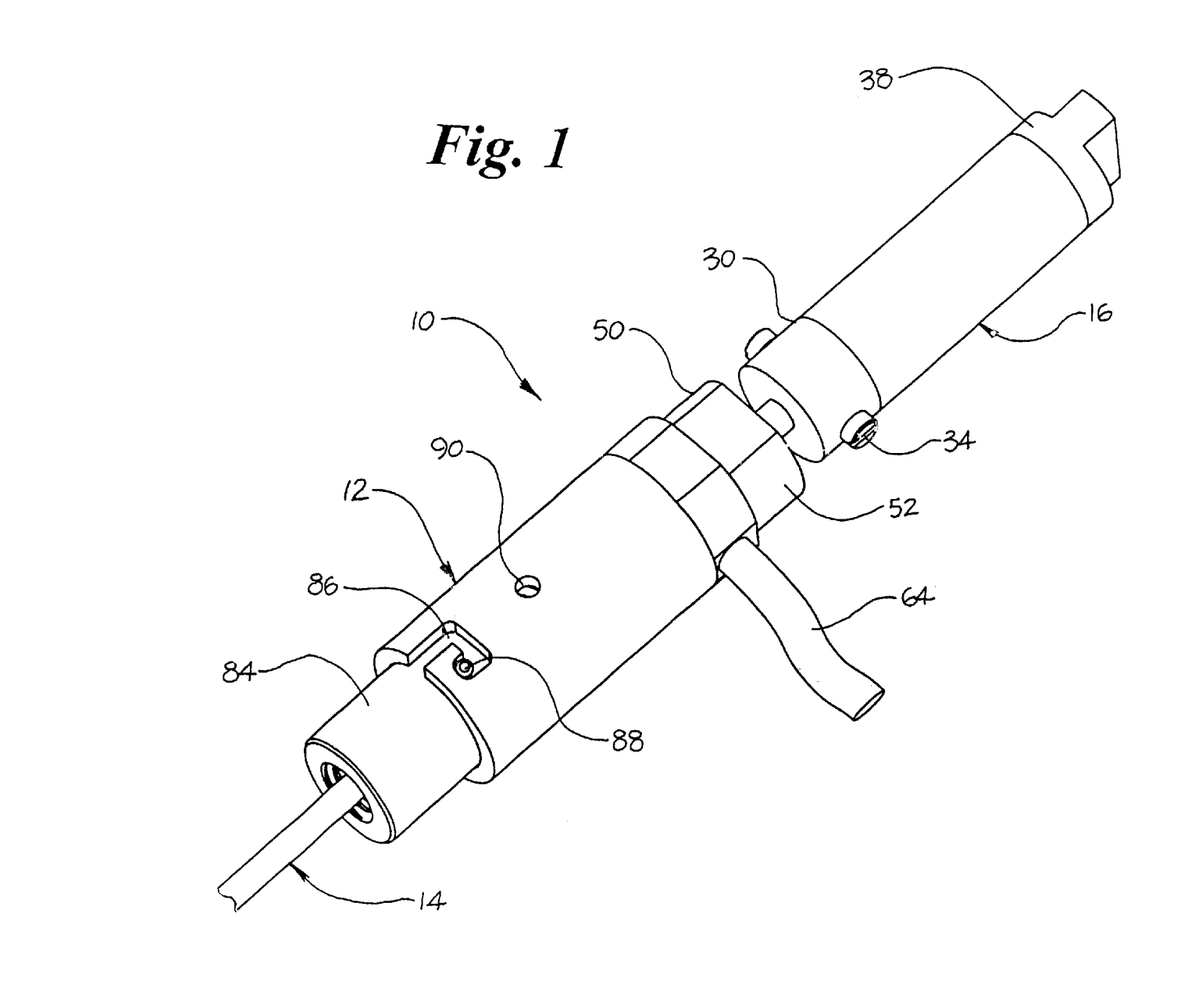
FIG. 1 is a perspective view of an embodiment of the invention.

Below the piston chamber 60, the housing 12 defines a biasing chamber 80. The biasing chamber 80 contains a biasing member or return spring 82 which is biased against the piston member 66 and a distal retaining collar 84. As may best be seen in FIG. 6, the distal retaining collar 84 may include one or more retaining projections 88 which project outwardly therefrom. The retaining projections 88 are received into a corresponding number of receiving channels 86 positioned in the housing 12, as is shown in FIG. 1. The arrangement of retaining projections 88 and receiving channels 86 provides the device 10 with the capacity to readily remove the retaining collar 84 thereby providing access to the various components discussed above contained within the housing 12. Alternatively, any variety of affixing means may be used to removably engage the distal retaining collar 84 to the housing 12. Such means may include, but are not limited to, screws and appropriately positioned holes, snap fit engagement of the collar 84 and housing 12, respectively reversed threads to allow the collar 84 to be threadingly received into the housing 12, etc.

Figure 6:
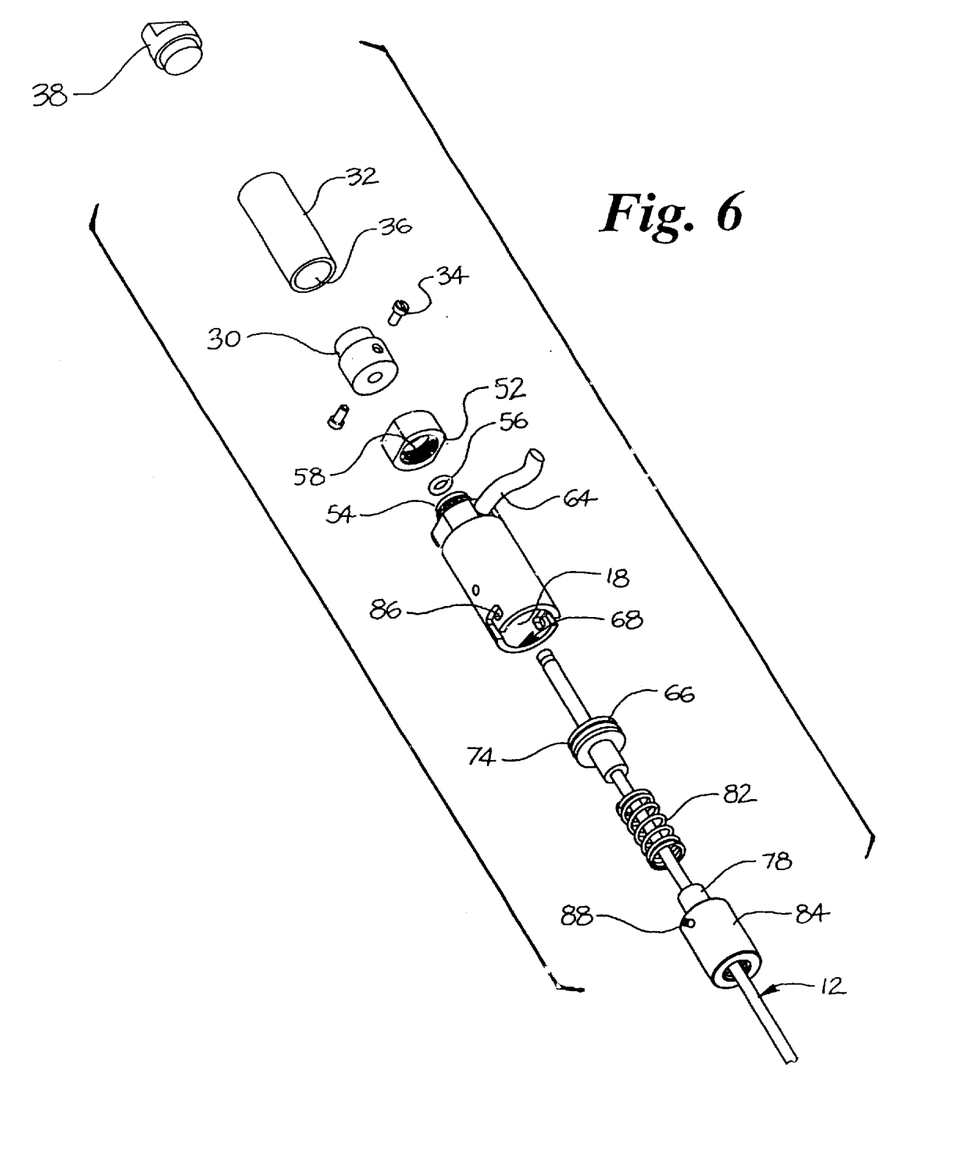
FIG. 6 is an exploded view of an embodiment of the invention.

As indicated above, the distal retaining collar 84 includes a proximally extending stop 78, shown in FIG. 6. The stop 78 is constructed and arranged to limit the distance the piston member 66 can move when subjected to fluid pressure as discussed.

The area between the distal retaining collar 84 and the piston member 66 defines the biasing chamber 80. When the piston member 66 is moved distally as a result of fluid pressure in the piston chamber 60, the biasing member 82 is compressed. After the biasing member 82 has moved to its full extent and is stopped by stop 78, the fluid pressure will continue to build until it is sufficient to break the seal of valve seals 55 and/or 75, thereby momentarily releasing the built up fluid pressure within the piston chamber 60. When the pressure is released in this manner, the biasing member 82 has sufficient force to push the piston member 66 proximally to its original at rest position or until fluid pressure is sufficient to once again overcome the biasing force supplied to the piston member 66 from the biasing member 82, subsequent to which the piston will again begin moving distally to repeat the cycle.

In order to allow for any compression of the biasing member 82, the wall 68 of the housing 12 includes a vent hole 90 which allows air to travel out of the biasing chamber 80 during compression of the biasing member 82 and back therein during its expansion.

The injection of fluid into the piston chamber 60 coupled with the resistance provided by biasing member 82, provides the device 10 with a needle 14 and reservoir 16 which moves in a longitudinally reciprocating motion relative to the housing 12. Such reciprocating motion is indicated by arrows 46 in FIG. 4

Figure 8:
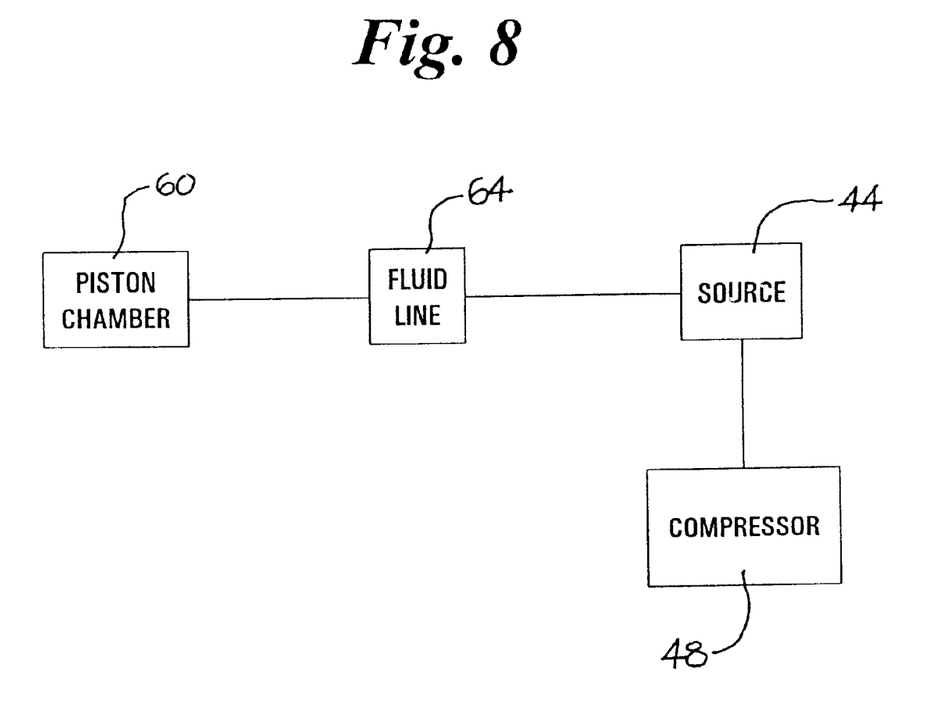
FIG. 8 is a block diagram illustrating the use of an embodiment of the invention.

The movement of the needle and reservoir may be varied depending on the rate which fluid is injected into the chamber 60. The rate may be selectively controlled by a pressure switch, toggle, button, knob, lever, or other controller device 48 connected to the device 10 and/or fluid source 44, such as is illustrated in FIG. 8. Preferably, the controller 48 is a foot pedal which is operatively engaged to the fluid source 44 or line 64.

As may be seen in FIG. 2, reciprocation of the needle 14 and reservoir 16 functions, in-part, to vibrate or agitate the reservoir 16 and the fill material 40 located therein. The vibration of the reservoir 16 ensures that only individual particles of fill material 40 are accepted into the slot 42 and eventually the needle chamber 20. If multiple particles somehow manage to enter the slot 42 simultaneously, or the slot 42, and/or needle chamber 20 become jammed with particles of fill material 40, the vibration of the reservoir 16 and needle 14 is sufficient to dislodge the particles and/or blockage.

The vibratory action of needle 14 and reservoir 16, when coupled with gravity ensures that the individual fill particles 40 which enter the needle chamber 20 will travel through its length to be deposited at the deposit site 96 as shown in FIGS. 4 and 5.

In addition to providing a vibratory action to the reservoir 16 and needle 14, the cyclic movement of the device 10 also provides the distal end of the needle 14 with a controlled tapping action which when applied to deposited fill material 40 compacts the fill material 40 without breaking or otherwise degrading the particles. As a result the fill material can be deposited loosely or extremely tight within the deposit site as desired.

In order to ensure that the hollow needle 14 does not enter into the operation site to an undesired depth, an adjustable depth guide 92 may be disposed about the needle 14, such as is shown in FIG. 5. The depth guide 92 is effectively a hollow tube or sheath through which the needle 14 passes. In the embodiment shown, the needle 14 does not contact the depth guide 92. However, the depth guide 92 may be in intermittent or constant contact with the needle 14. If the device is constructed in such a manner that the depth guide 92 and needle 14 may be in contact with one another, or are in contact with one another, a biocompatible lubricant may be applied to the internal surface of the depth guide 92 to ensure minimalization of friction created by the contact between the moving needle 14 and depth guide 92.

As may be seen in FIG. 5, depth guide 92 may be adjustable to provide the operating surgeon or technician with the ability to set the length of the needle 14 which may enter into the operating site 96 during reciprocation of the needle 14. In the embodiment shown, the proximal end 98 of the depth guide 92 is threadingly engaged to the distal retaining collar 84 or other portion of the housing 12. By rotating the depth guide 92 about the threads 94, the depth guide 92 may be extended or retracted relative to the needle 14. Alternatively, the depth guide 92 may be slidingly or otherwise adjustably engaged to the housing 12 or a portion thereof.

At the distal end 102 of depth guide 92 there may be a contact member 100 which is sized to engage the opening or area of tissue adjacent to the opening of the operation site 96. The contact member may be integral with the depth guide 92 or may be permanently or removably attached thereto by a snap-fit, threading, sliding, or any other suitable attachment means or methods. Contact member 100 may be constructed from any material suitable for use in a surgical device. It is preferable however, that contact member 100 be constructed from one or more material which may have vibration absorbing properties such as rubber, silicon or other vibration dampening materials. In addition to contact member 100, sheath 92 as well as other portions of device 10 may include, or be constructed at least partially from vibration absorbing materials.

The shape and size of the contact member 100 are such that the contact member may be placed against and supported by the tissue surrounding the opening of the operation site 96. When placed about the operation site 96 in such a manner, the contact member 100 provides a stable point of reference which the operating surgeon may use to determine, adjust and set the depth, or potential depth, of the needle 14 into the operating site 96.

By providing the device 10 with a depth gauge 92 and contact member 100, the depth of the needle 14 into the operation site 96 may be established with accuracy. As a result, the tapping and compacting action of the reciprocating needle 14 against the fill material 40 may be precisely controlled. Such control will allow an operator to control or avoid inadvertent fracture or other potential damage to the particles of fill material 40. In addition, inadvertent contact with the tissue of the operating site 96 may also be reduced.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims.

What is claimed is:

1. A device for inserting particles of fill material into a body cavity comprising:

a reservoir, the reservoir defining a chamber, the chamber constructed and arranged to contain a predetermined volume of the particles of fill material, the reservoir defining an opening at one end through which the particles may exit the chamber, the opening constructed and arranged to allow only one particle at a time to exit the chamber;

an injection cylinder, the injection cylinder having a proximal end and a distal end, the proximal end being engaged to the reservoir, the injection cylinder defining a hollow chamber being open at both ends, the proximal end of the injection cylinder being coupled to the reservoir thereby defining a coupled assembly, the hollow chamber being in fluid communication with the opening, the hollow chamber sized to receive the particles from the opening and pass the particles therethrough; and a reciprocator device, the reciprocator device operatively engaged to at least a portion of the injection cylinder, the reciprocator device constructed and arranged to reciprocatingly move the coupled assembly thereby causing the particles of fill material to exit the chamber through the opening one particle at a time and pass the particles through the hollow chamber; wherein the reciprocator device defines a longitudinally oriented hollow passage which extends therethrough, the injector cylinder having a piston member fixedly engaged thereto, the reciprocator device being constructed and arranged to reciprocatingly move the piston member between a first position and a second position within a first portion of the longitudinally oriented hollow passage.

2. The device of claim 1 wherein the piston member further comprises a slidable piston seal, the slidable piston seal slidably sealing the piston member to the first portion of the longitudinally oriented hollow passage.

3. The device of claim 2 wherein the longitudinally oriented hollow passage further comprises a proximal sliding seal assembly, the proximal sliding seal assembly slidably sealing the injection cylinder proximal to the piston member to a proximal opening of the first portion of the longitudinally oriented hollow passage.

4. The device of claim 3 wherein reciprocator device further comprises a fluid injection port, the fluid injection port being positioned proximal of the piston member and providing fluid communication between the first portion of the longitudinally oriented hollow passage and a fluid source.

5. The device of claim 4 wherein the fluid source is constructed and arranged to selectively inject a fluid into the first portion of the longitudinally oriented hollow passage through the fluid injection port, the fluid providing a sufficient pressure to move the piston member from the first position to the second position.

6. The device of claim 5 further comprising a biasing member, the biasing member being positioned in a second portion of the longitudinally oriented hollow passage distally positioned relative to the first portion of the longitudinally oriented hollow passage, the biasing member being biasedly engaged between the piston member and a distal stop member, the biasing member exerting a sufficient biasing force to move the piston member from the second position to the first position.

7. The device of claim 6 wherein the distal stop member is engaged to a distal end of the reciprocator device, the distal stop member defining an opening, the opening of the distal stop member having a diameter sized to slidingly pass the cylindrical injector therethrough, the opening of the distal stop member having a diameter smaller than the piston member.

8. The device of claim 7 wherein the distal stop member is removably engaged to the distal end of the reciprocator device.

9. The device of claim 8 wherein the distal stop member further comprises at least one engagement member, the at least one engagement member constructed and arranged to be removably engaged to a distal end of the reciprocator device.

10. The device of claim 9 wherein the distal end of the reciprocator device comprises at least one engagement channel, the at least one engagement channel constructed and arranged to removably receive the at least one engagement member.

11. The device of claim 5 wherein the fluid source is a fluid pump selected from the group consisting of a pneumatic pump, a hydraulic pump, and any combination thereof.

12. The device of claim 5 further comprising a controller device, the controller device constructed and arranged to selectively control the flow of fluid from the fluid source into the first portion of the longitudinally oriented hollow passage.

13. The device of claim 3 wherein the proximal sliding seal assembly is constructed and arranged to release fluid pressure from the first portion of the longitudinally oriented hollow passage after the piston member is moved from the first position to the second position therein.

14. A device for inserting particles of fill material into a body cavity comprising:
a reservoir, the reservoir defining a chamber, the chamber constructed and arranged to contain a predetermined volume of the particles of fill material, the reservoir defining an opening at one end through which the particles may exit the chamber, the opening constructed and arranged to allow only one particle at a time to exit the chamber;
an injection cylinder, the injection cylinder having a proximal end and a distal end, the proximal end being engaged to the reservoir, the injection cylinder defining a hollow chamber being open at both ends, the proximal end of the injection cylinder being coupled to the reservoir thereby defining a coupled assembly, the hollow chamber being in fluid communication with the opening, the hollow chamber sized to receive the particles from the opening and pass the particles therethrough;
a reciprocator device, the reciprocator device operatively engaged to at least a portion of the injection cylinder, the reciprocator device constructed and arranged to reciprocatingly move the coupled assembly thereby causing the particles of fill material to exit the chamber through the opening one particle at a time and pass the particles through the hollow chamber; and
further comprising a depth guide, the depth guide defining a sheath, the sheath being disposed about at least a portion of the injection cylinder, a proximal end of the depth guide being engaged to at least a portion of the reciprocator device, whereby when the reciprocator device reciprocatingly moves the coupled assembly the depth guide remains substantially immobile relative to the injection cylinder and the depth guide is adjustably engaged to the at least a portion of the reciprocator device.

15. The device of claim 14 wherein the depth guide is threadingly engaged to the at least a portion of the reciprocator device.

16. A device for inserting particles of fill material into a body cavity comprising:
a reservoir, the reservoir defining a chamber, the chamber constructed and arranged to contain a predetermined volume of the particles of fill material, the reservoir defining an opening at one end through which the particles may exit the chamber, the opening constructed and arranged to allow only one particle at a time to exit the chamber;
an injection cylinder, the injection cylinder having a proximal end and a distal end, the proximal end being engaged to the reservoir, the injection cylinder defining a hollow chamber being open at both ends, the proximal end of the injection cylinder being coupled to the reservoir thereby defining a coupled assembly, the hollow chamber being in fluid communication with the opening, the hollow chamber sized to receive the particles from the opening and pass the particles therethrough; and a reciprocator device, the reciprocator device operatively engaged to at least a portion of the injection cylinder, the reciprocator device constructed and arranged to reciprocatingly move the coupled assembly thereby causing the particles of fill material to exit the chamber through the opening one particle at a time and pass the particles through the hollow chamber; further comprising a depth guide, the depth guide defining a sheath, the sheath being disposed about at least a portion of the injection cylinder, a proximal end of the depth guide being engaged to at least a portion of the reciprocator device, whereby when the reciprocator device reciprocatingly moves the coupled assembly the depth guide remains substantially immobile relative to the injection cylinder; wherein the depth guide further comprises a distal end, the distal end having a contact member engaged thereto, the contact member constructed and arranged to be disposed about at least a portion of an opening of an operating site, wherein the contact member is removably engaged to the distal end of the depth guide.

17. The device of claim 16 wherein the contact member is constructed at least partially from a vibration absorbing material.

18. A device for inserting particles of fill material into a body cavity comprising:

a reservoir, the reservoir defining a chamber, the chamber constructed and arranged to contain a predetermined volume of the particles of fill material, the reservoir defining an opening at one end through which the particles may exit the chamber, the opening constructed and arranged to allow only one particle at a time to exit the chamber;

an injection cylinder, the injection cylinder having a proximal end and a distal end, the proximal end being engaged to the reservoir, the injection cylinder defining a hollow chamber being open at both ends, the proximal end of the injection cylinder being coupled to the reservoir thereby defining a coupled assembly, the hollow chamber being in fluid communication with the opening, the hollow chamber sized to receive the particles from the opening and pass the particles therethrough; and a reciprocator device, the reciprocator device operatively engaged to at least a portion of the injection cylinder, the reciprocator device constructed and arranged to reciprocatingly move the coupled assembly thereby causing the particles of fill material to exit the chamber through the opening one particle at a time and pass the particles through the hollow chamber; further comprising a depth guide, the depth guide defining a sheath, the sheath being disposed about at least a portion of the injection cylinder, a proximal end of the depth guide being engaged to at least a portion of the reciprocator device, whereby when the reciprocator device reciprocatingly moves the coupled assembly the depth guide remains substantially immobile relative to the injection cylinder, wherein the depth guide and the injection cylinder have a lubricant therebetween.

19. The device of claim 18 wherein the lubricant is biocompatible.

20. A device for inserting fill material into a body cavity comprising:

a hollow injection cylinder, a reservoir for containing the fill material, and a central housing, the hollow injection cylinder being in fluid communication with the reservoir, the central housing defining a passage which extends therethrough, the passage being disposed about the hollow injection cylinder, the hollow injection cylinder being longitudinally moveable within the passage, the hollow injection cylinder and the central housing having at least one sliding valve seal therebetween;

at least a portion of the hollow injection cylinder having a piston member fixedly engaged thereto, the piston member having a first position and being moveable to a second position, a first portion of the passage defining a piston chamber, the piston chamber constructed and arranged to receive a predetermined quantity of fluid therein, the predetermined quantity of fluid exerting a distally acting force on the piston member;

a second portion of the passage defining a biasing chamber, the biasing chamber having a biasing member disposed between the piston member and a distal surface, the biasing member exerting a proximally acting biasing force on the piston member;

whereby, when the predetermined quantity of fluid is received into the chamber, the first distally acting force is sufficient to move the piston member in the distal direction from the first position to the second position, after the piston member is moved to the second position at least a portion of the predetermined quantity of fluid is released, thereinafter the proximally acting force is sufficient to return the piston member from the second position to the first position.

\* \* \* \* \*